United States Patent
Lee et al.

(10) Patent No.: US 11,268,953 B2
(45) Date of Patent: Mar. 8, 2022

(54) REAGENT COMPOSITION FOR MEASURING GLYCATED HEMOGLOBIN AND METHOD FOR MEASURING GLYCATED HEMOGLOBIN USING SAME

(71) Applicant: DXGEN CORP., Gunpo-si (KR)

(72) Inventors: Jin Woo Lee, Suwon-si (KR); Seon Ah Cheon, Seoul (KR)

(73) Assignee: DXGEN CORP., Gyeonggi-Do (KR)

( * ) Notice: Subject to any disclaimer, the term of this patent is extended or adjusted under 35 U.S.C. 154(b) by 383 days.

(21) Appl. No.: 16/335,396

(22) PCT Filed: Sep. 22, 2017

(86) PCT No.: PCT/KR2017/010497
§ 371 (c)(1),
(2) Date: Mar. 21, 2019

(87) PCT Pub. No.: WO2018/056761
PCT Pub. Date: Mar. 29, 2018

(65) Prior Publication Data
US 2019/0285622 A1 Sep. 19, 2019

(30) Foreign Application Priority Data

Sep. 22, 2016 (KR) .................. 10-2016-0121689
Sep. 21, 2017 (KR) .................. 10-2017-0122083

(51) Int. Cl.
*G01N 21/55* (2014.01)
*G01N 21/77* (2006.01)
(Continued)

(52) U.S. Cl.
CPC ....... *G01N 33/54346* (2013.01); *G01N 21/55* (2013.01); *G01N 21/77* (2013.01);
(Continued)

(58) Field of Classification Search
CPC .. G01N 33/54346; G01N 33/52; G01N 21/55; G01N 21/77; G01N 33/723; G01N 2800/042
See application file for complete search history.

(56) References Cited

U.S. PATENT DOCUMENTS 5,631,364 A 5/1997 Sundrehagen et al.
5,919,708 A 7/1999 Sundrehagen
(Continued)

FOREIGN PATENT DOCUMENTS

EP 2444803 A1 4/2012
KR 10-2008-0023280 A 3/2008
(Continued)

OTHER PUBLICATIONS

Wang, Jiasheng et al., "Silica-based nanocomposites via reverse microemulsions: classifications, preparations, and applications", Nanoscale, 2014, pp. 4418-4437, vol. 6, No. 9.
(Continued)

*Primary Examiner* — Jennifer Wecker
*Assistant Examiner* — Michael Paul Shimek
(74) *Attorney, Agent, or Firm* — Novick, Kim & Lee, PLLC; Jae Youn Kim (57) ABSTRACT

Provided is a reagent composition for measuring glycated hemoglobin to diagnose the presence or absence of diabetes and a method of measuring glycated hemoglobin using the same, and more particularly is a reagent composition for measuring glycated hemoglobin, the composition including a dye-encapsulated silica nanoparticle-boronic acid, and to a method of measuring glycated hemoglobin using the same. In the reagent composition for measuring the glycated hemoglobin, since a dye is encapsulated in silica nanoparticles, the inherent absorption wavelength of the dye is not
(Continued)

affected by pH and the composition has excellent stability even when stored for one month or more.

8 Claims, 4 Drawing Sheets

(51) Int. Cl.
 *G01N 33/52* (2006.01)
 *G01N 33/543* (2006.01)
 *G01N 33/72* (2006.01)
(52) U.S. Cl.
 CPC .......... *G01N 33/52* (2013.01); *G01N 33/723* (2013.01); *G01N 2800/042* (2013.01)

(56) References Cited

U.S. PATENT DOCUMENTS

| | | |
|---|---|---|
| 7,374,943 B2 | 5/2008 | Holtlund et al. |
| 2003/0073243 A1 | 4/2003 | Law et al. |
| 2004/0137641 A1* | 7/2004 | Holtlund ............ G01N 33/6842 436/514 |
| 2008/0063868 A1* | 3/2008 | Chung .................... C09C 1/309 428/402 |

FOREIGN PATENT DOCUMENTS

| | | |
|---|---|---|
| KR | 10-2010-0137851 A | 12/2010 |
| KR | 1128037 B1 | 3/2012 |
| WO | 2014-033258 A1 | 3/2014 |
| WO | WO-2014033258 A1 * | 3/2014 ........... G01N 33/723 |

OTHER PUBLICATIONS

Lin Wang et al., "Watching Silica Nanoparticles Glow in the Biological World", Analytical Chemistry, American Chemical Society, Feb. 2006 (Feb. 1, 2006), pp. 646-654, vol. 78, No. 3.

\* cited by examiner

REAGENT COMPOSITION FOR MEASURING GLYCATED HEMOGLOBIN AND METHOD FOR MEASURING GLYCATED HEMOGLOBIN USING SAME

TECHNICAL FIELD

The present invention relates to a reagent composition for measuring glycated hemoglobin to diagnose the presence or absence of diabetes and a method of measuring glycated hemoglobin using the same, and more particularly to a reagent composition for measuring glycated hemoglobin, the composition including a dye-encapsulated silica nanoparticle-boronic acid, and to a method of measuring glycated hemoglobin using the same.

BACKGROUND ART

Diabetes is a metabolic disease caused by an abnormality of insulin, which plays a role in regulating blood sugar. It is classified into Type 1 diabetes, which occurs due to insulin deficiency when insulin-producing cells are destroyed due to an abnormality in the immune system, and Type 2 diabetes, caused by a lack of insulin secretion or an ineffective use of insulin, depending on the cause of a disease.

Diabetes is characterized by hyperglycemia, in which the glucose concentration in the blood is elevated. Failure to control blood glucose may lead to complications such as diabetic retinopathy, kidney disease, and foot lesions. Therefore, the importance of blood glucose management for diabetics is increasing.

Conventional diabetes measurement markers use glucose. However, since blood glucose fluctuates greatly before and after a meal, there are problems in that error due to the measurement time and fluctuation due to the condition of the patient may be very evident. Further, measurement of glucose oxidase, used for glucose measurement, may be vulnerable to environmental influences such as pH or other interfering materials contained in the blood, and hydrogen peroxide may be generated, thus affecting enzyme activity.

Therefore, recently, glycated hemoglobin (HbA1c) has been used as a biomarker that more accurately and stably determines a blood glucose level compared to glucose. Once glycated hemoglobin is generated, it is stable until erythrocytes disappear. Therefore, since glycated hemoglobin may be used as an indicator for showing the mean blood glucose level over 2 to 3 months, it is used to diagnose and investigate the progress of diabetes treatment in practice. However, there is a problem in that a glycated-hemoglobin measurement method is not suited to patients of some diseases that make it difficult to maintain constant blood glucose, as in terminal chronic renal failure or patients with erythrocyte abnormalities.

In order to diagnose diabetes using glycated hemoglobin, it is necessary to judge the amount of glycated hemoglobin relative to the amount of total hemoglobin instead of the absolute value of glycated hemoglobin, because the amounts of total hemoglobin of individuals are different depending on sex, age, and blood-related diseases. Therefore, in order to use glycated hemoglobin as a diagnostic indicator for diabetes, a technique capable of distinguishing the amount of total hemoglobin and the amount of glycated hemoglobin is necessary.

Hemoglobin includes heme, in the center of which iron ions are coordinated, and globin proteins. The hemoglobin has an absorption wavelength of 400 to 600 nm, which varies slightly depending on chemical modification such as the binding of hemoglobin to oxygen and the methylation thereof. Among the absorption wavelengths, an absorption wavelength of 430 nm is a common characteristic of glycated hemoglobin and general hemoglobin, so a measurement thereof may be used to indicate the amount of total hemoglobin. Accordingly, it is necessary to selectively label only glycated hemoglobin in order to distinguish the same. For this purpose, a boronic acid-affinity method is used. This is a method in which a coloring dye or a fluorescent material is bound to boronic acid for recognizing cis-diol at the glucose site of glycated hemoglobin and is then used as a label. The method is excellent in sensitivity and stability, like a reaction adopting an enzyme or an antigen-antibody reaction.

U.S. Pat. Nos. 5,631,364 and 7,374,943 and International Patent No. 2014-033258 disclose a method that includes reacting a dye-binding boronic acid derivative with a glycated hemoglobin in the blood, loading the resultant substance on a cartridge including a porous filter paper, performing washing, and measuring the reflectances (%) of total hemoglobin and dye-binding glycated hemoglobin, thereby determining the ratios of the two materials.

However, there are problems in that boronic acid derivatives conjugated with a dye are vulnerable to light and heat because they are directly exposed to the external environment and in that a synthesis process thereof is complicated. Most organic-based dye molecules have a problem in that the coloring amount and coloring wavelength are changed or in that light is sometimes extinguished thereby depending on the pH or polarity of the reaction system and the surrounding environment, such as other impurities. Accordingly, there is a need for a method for minimizing the effect of the same.

Meanwhile, European Patent No. 2444803 and Korean Patent No. 1128037 disclose a method of enabling boronic acid derivatives to bind to beads and a method of measuring glycated hemoglobin by directly loading a reacted sample on a cartridge including a porous filter paper. Although the synthesis of beads and boronic acid derivatives is relatively simple, since the same wavelength region of hemoglobin and glycated hemoglobin is measured, total hemoglobin is first measured, and the number of hemoglobin reacted with the bead-boronic acid derivative is measured. In order to remove normal hemoglobin, it is required to perform a cumbersome process for measuring the remaining glycated hemoglobin after washing. Further, since the same wavelength range is measured, caution must be taken to wash away the normal hemoglobin.

As a result of efforts made to solve the above problems, the inventors of the present invention have found that when using boronic acid conjugated with dye-encapsulated silica nanoparticles having different absorption spectra from hemoglobin or modified hemoglobin, the amounts of hemoglobin and glycated hemoglobin are capable of being measured quickly and accurately in a simple and stable manner using an optical instrument, whereby the present invention has been completed.

DISCLOSURE

Technical Problem

An object of the present invention is to provide a reagent composition for measuring glycated hemoglobin to simply and accurately diagnose the presence or absence of diabetes, and a method of measuring glycated hemoglobin using the same.

Technical Solution

In order to accomplish the above object, the present invention provides a reagent composition for measuring glycated hemoglobin. The reagent composition includes ① a hemolytic liquid and ② a "dye-encapsulated silica nanoparticle-boronic acid" specifically binding to the glycated hemoglobin.

The present invention also provides a method of measuring glycated hemoglobin. The method includes (a) introducing a blood sample into a reagent composition for measuring the glycated hemoglobin, the composition including ① a hemolytic liquid and ② a "dye-encapsulated silica nanoparticle-boronic acid" specifically binding to the glycated hemoglobin, followed by hemolysis and reaction, (b) injecting a reactant into an absorption pad of a cartridge, followed by washing with a washing liquid, (c) measuring an optical reflectance of the absorption pad using an optical instrument to measure the amounts of total hemoglobin and glycated hemoglobin, and (d) calculating a ratio of the glycated hemoglobin on the basis of the measured amounts of the total hemoglobin and the glycated hemoglobin.

In the present invention, the hemolytic liquid is selected from the group consisting of TRIS, HEPES, TES, MOPS, and PIPES.

In the present invention, a dye encapsulated in silica nanoparticles is a blue-colored dye, and is selected from the group consisting of xylene cyanol FF (acid blue 147), methylene blue, bromophenol blue, malachite green, bromocresol green, Azure A, and indigo blue.

In the present invention, "dye-encapsulated silica nanoparticles" are manufactured by adding a dye and silica to a mixture solution of water and a surfactant or a mixture solution of water and an organic solvent, followed by agitation and addition of a basic catalyst, and specifically bind to the glycated hemoglobin.

In the present invention, the diameter of "dye-encapsulated silica nanoparticles" is 10 to 500 nm.

In the present invention, the "dye-encapsulated silica nanoparticle-boronic acid" is manufactured by aminating "dye-encapsulated silica nanoparticles", followed by conjugation with 4-carboxylicphenyl boronic acid (CPBA), or by carboxylating or aldehyding the "dye-encapsulated silica nanoparticles", followed by conjugation with 3-aminophenylboronic acid (APBA).

In the present invention, the optical instrument radiates a wavelength for measuring the total hemoglobin and a wavelength for measuring the glycated hemoglobin binding to the "dye-encapsulated silica nanoparticle-boronic acid" as light sources, thus measuring the optical reflectance.

In the present invention, in the method of measuring the glycated hemoglobin, diabetes is diagnosed according to the ratio of the glycated hemoglobin.

Advantageous Effects

In a reagent composition for measuring glycated hemoglobin according to the present invention, since a dye is encapsulated in silica nanoparticles, the inherent absorption wavelength of the dye is not affected by pH and the composition has excellent stability even when stored for one month or more. A plurality of dye molecules is encapsulated in a single silica nanoparticle, so that the amount of light absorbed by one particle is larger than that absorbed by one dye molecule.

Accordingly, it is possible to accurately measure the amount of glycated hemoglobin in the blood, which conventionally has a low detection limit.

BEST MODE

In the present invention, the intention is to confirm that when using boronic acid conjugated with dye-encapsulated silica nanoparticles having absorption spectra different from hemoglobin or modified hemoglobin, the amounts of hemoglobin and glycated hemoglobin are capable of being measured accurately in a simple and stable manner using an optical instrument.

In the present invention, a "dye-encapsulated silica nanoparticle-boronic acid" specifically binding to glycated hemoglobin was manufactured, and a hemolytic liquid was added thereto, thus manufacturing a reagent composition for measuring glycated hemoglobin. Next, a blood sample was added to the manufactured reagent composition to perform hemolysis and reaction, and was then injected into an absorption pad, followed by washing. The optical reflectance of the absorption pad was measured using the optical instrument in order to measure the amounts of total hemoglobin and glycated hemoglobin. As a result, it was confirmed that it was possible to diagnose diabetes simply and quickly using the ratio of glycated hemoglobin.

That is, in an embodiment of the present invention, a blue-colored methylene blue dye was encapsulated in silica nanoparticles, the hydroxyl group (—OH) on the surface thereof was substituted with a primary amine group, and 4-carboxylicphenyl-boronic acid (CPBA), which is a glycated hemoglobin-binding material, was fixed to the surface thereof, thus manufacturing a "methylene blue-encapsulated silica nanoparticle-boronic acid". The methylene blue-encapsulated silica nanoparticle-boronic acid was mixed with the hemolytic liquid for hemolysis of the blood sample, thus manufacturing a reagent composition for measuring glycated hemoglobin. Next, the blood sample was added to the manufactured reagent composition to perform hemolysis and reaction, and was then injected into the absorption pad, followed by washing. Red (430 nm) and blue (650 to 700 nm) light sources were radiated on the absorption pad using the optical instrument to thus measure the optical reflectance of total hemoglobin and glycated hemoglobin labeled with the dye. Thereby, it could be confirmed that the ratio of glycated hemoglobin was capable of being measured simply and quickly.

Therefore, in an aspect, the present invention relates to a reagent composition for measuring glycated hemoglobin, the composition including ① a hemolytic liquid and ② a "dye-encapsulated silica nanoparticle-boronic acid" specifically binding to glycated hemoglobin.

Since the concentration of glycated hemoglobin in the blood sample is measured relative to the amount of total hemoglobin in the blood, in order to measure the concentration of glycated hemoglobin, the blood sample must first be hemolyzed to thus expose normal hemoglobin and glycated hemoglobin contained in the blood.

In the present invention, any hemolytic liquid may be used without limitation, as long as the hemolytic liquid has a buffer concentration at osmotic pressure at which hemolysis is feasible, and examples thereof may include TRIS, HEPES, MOPS, TES, and PIPES, each having a pH of 7 to 8.5. The blood sample that is hemolyzed includes hemoglobin and glycated hemoglobin together.

Figure 1:
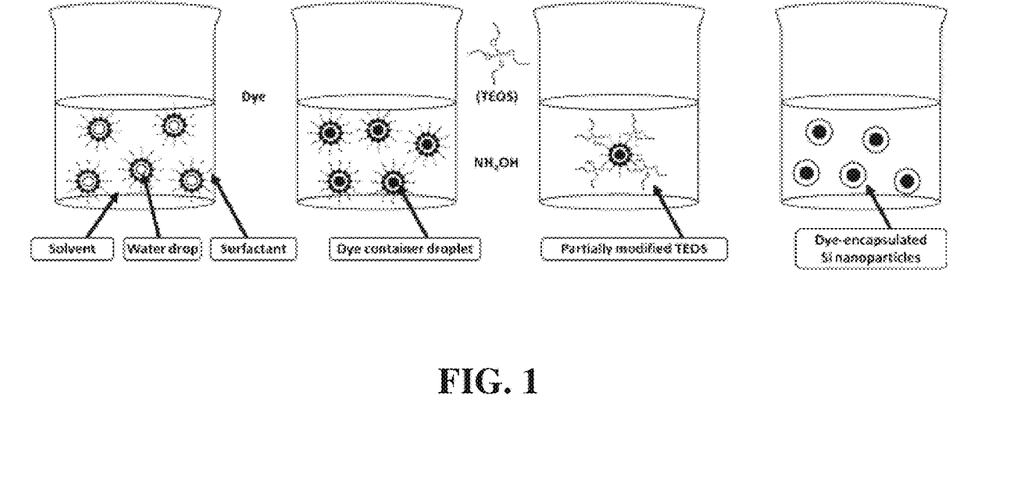
FIG. 1 is a view showing a method of manufacturing "dye-encapsulated silica nanoparticles" according to an embodiment of the present invention.

As shown in FIG. 1, the "dye-encapsulated silica nanoparticles" may be manufactured by adding a dye and silica to a mixture solution of water and a surfactant or a mixture solution of water and an organic solvent, followed by agitation and then addition of a basic catalyst.

In the present invention, the dye encapsulated in the silica nanoparticles is preferably a blue-colored dye (blue dye, BD) having a value larger than 400 to 600 nm, within which the entire spectrum of all red hemoglobin, including hemoglobin and glycated hemoglobin, appears. Preferable examples thereof include xylene cyanol FF (acid blue 147), methylene blue, bromophenol blue, malachite green, bromocresol green, Azure A, and indigo blue. Methylated hemoglobin, which is present in a small number and which appears at 620 to 630 nm, may be excluded. The dye is more preferably methylene blue at 660 nm, which may maintain a blue color even under a basic condition of pH of 9 or more, at which the synthesis of silica nanoparticles is performed.

The surfactant is not particularly limited, but triton x-100 or n-hexane may be used in the present invention. Examples of the silica may include tetraethyl orthosilicate or tetramethyl orthosilicate.

The basic catalyst is to promote the encapsulation of the dye by a silica precursor, which may promote the hydrolysis of water and the silica precursor. The ionized silica precursors react with each other to thus produce water and alcohol (ROH), which are connected to each other to thus form a silica network and grow.

Examples of the basic catalyst may include ammonium hydroxide, tetrapropylammonium chloride, tetrapropylammonium hydroxide, tetrabutylammonium bromide, tetrabutylammonium chloride, or tetrabutylammonium hydroxide.

In the case of the "dye-encapsulated silica nanoparticles", since the dye does not leak to the outside, stability and sensitivity may be increased, bio-toxicity may be low, and the functional groups on the surface thereof may be easily changed.

The diameter of the "dye-encapsulated silica nanoparticles" may be 10 to 500 nm, and preferably 30 to 100 nm, which makes it possible to maintain the inherent properties of the dye. When the diameter is less than 10 nm, it is difficult to perform the operation. When the diameter is more than 500 nm, since the thickness thereof is increased, the dye may appear cloudy.

As boronic acid derivatives for imparting selectivity for glycated hemoglobin to the "dye-encapsulated silica nanoparticles", it is preferable to use 4-carboxylicphenyl boronic acid (CPBA) and 3-aminophenyl boronic acid (APBA). When the CPBA is used, the "dye-encapsulated silica nanoparticles" may be aminated. When the APBA is used, after the "dye-encapsulated silica nanoparticles" are carboxylated, conjugation may be performed via carbodiimide cross-coupling. Since the 4-carboxylicphenyl boronic acid (CPBA) has relatively higher thermal stability than the 3-aminophenyl boronic acid (APBA), it is preferable to use the CPBA.

Figure 2:
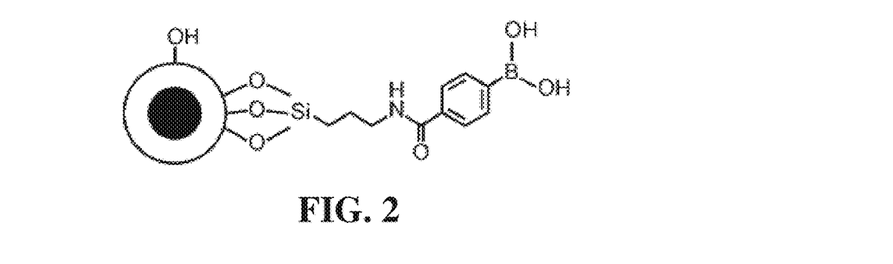
FIG. 2 shows the structure of a "dye-encapsulated silica nanoparticle-boronic acid" manufactured according to the embodiment of the present invention.
Figure 3:
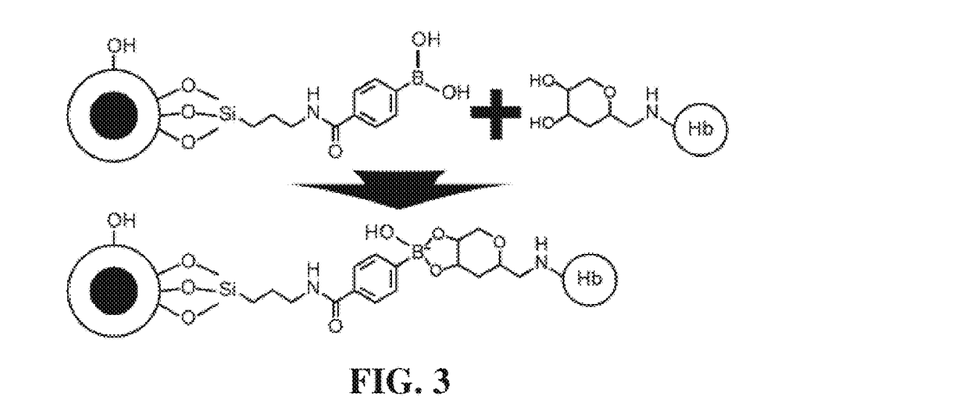
FIG. 3 is a view showing a binding reaction of the "dye-encapsulated silica nanoparticle-boronic acid" and glycated hemoglobin according to the embodiment of the present invention.

As shown in FIGS. 2 and 3, the "dye-encapsulated silica nanoparticle-boronic acid" may react with the cis-diol of glycated hemoglobin. A plurality of dye molecules is encapsulated in the silica nanoparticles, so that the amount of light absorbed by one particle is larger than that absorbed by one dye molecule. Accordingly, the detection limit of glycated hemoglobin may be improved.

Accordingly, in another aspect, the present invention relates to a method of measuring glycated hemoglobin. The method includes (a) introducing a blood sample into a reagent composition for measuring the glycated hemoglobin, the composition including ① a hemolytic liquid and ② a "dye-encapsulated silica nanoparticle-boronic acid" specifically binding to the glycated hemoglobin, followed by hemolysis and reaction, (b) injecting a reactant into an absorption pad of a cartridge, followed by washing with a washing liquid, (c) measuring an optical reflectance of the absorption pad using an optical instrument to measure the amounts of total hemoglobin and glycated hemoglobin, and (d) calculating a ratio of the glycated hemoglobin on the basis of the measured amounts of the total hemoglobin and the glycated hemoglobin.

Figure 4:
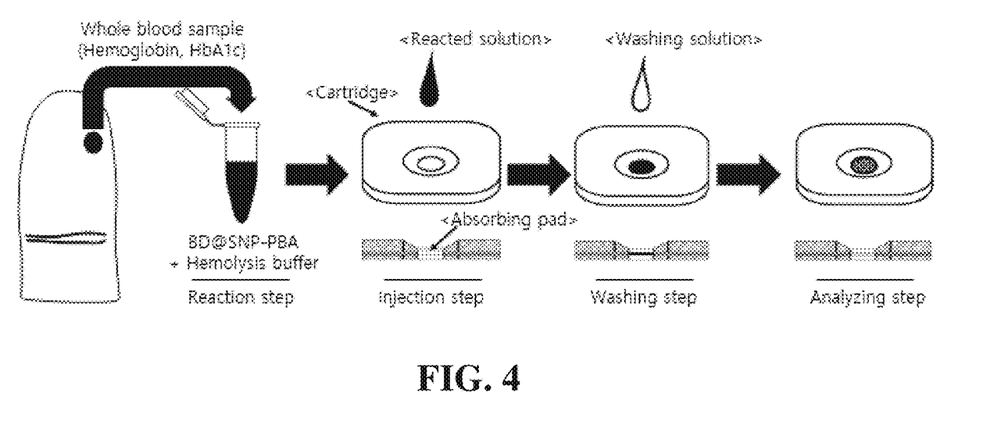
FIG. 4 is a flowchart showing a method of measuring glycated hemoglobin using a reagent composition for measuring glycated hemoglobin and an optical instrument of the present invention.
Figure 5:
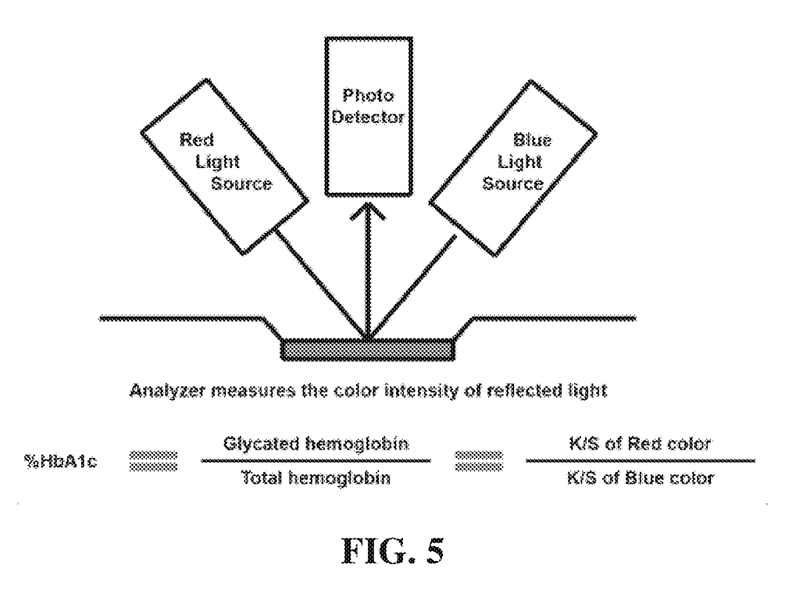
FIG. 5 is a view showing a radiation method of the optical instrument according to the embodiment of the present invention.

As shown in FIGS. 4 and 5, any optical instrument may be used without particular limitation as long as the optical instrument can measure optical reflectance using optical properties. The optical instrument may simultaneously radiate a wavelength for measuring total hemoglobin and a specific wavelength of the "dye(blue)-encapsulated silica nanoparticle-boronic acid" as light sources (e.g.: red (430 nm) and blue (650 to 700 nm)), and may measure the reflected optical signal using a photodiode detector (PD), thereby measuring the amounts of hemoglobin and glycated hemoglobin using an optical signal converter.

The ratio of glycated hemoglobin may be obtained by calculating the amount of glycated hemoglobin relative to the amount of total hemoglobin using the following equation.

Ratio (%) of glycated hemoglobin=glycated hemoglobin/total hemoglobin

Generally, in the case when the ratio of glycated hemoglobin is 6.5% or more, the case may be diagnosed as diabetes.

MODE FOR INVENTION

Hereinafter, the present invention will be described in more detail with reference to Examples. It is to be understood by those skilled in the art that these Examples are only for illustrating the present invention and that the scope of the present invention is not to be construed as being limited by these Examples.

Example 1: Manufacture of Blue Dye-Encapsulated Silica Nanoparticle-Boronic Acid (BD @SNP-CPBA)

1-1: Synthesis of Blue Dye-Encapsulated Silica Nanoparticles (BD @SNP)

135.0 ml of cyclohexane, 31.8 ml of Triton X-100, 32.4 ml of n-hexanol, 6.12 ml of 0.1 M methylene blue, and 2.7 ml of TEOS (tetraethyl orthosilicate) were added to a 1 L round bottom flask, and uniformly mixed for 1 hour using an agitator. 1.08 ml of 25-30% aqueous ammonia ($NH_4OH$) was added thereto and reacted at room temperature for 24 hours. 200 ml of ethanol was then added to terminate the reaction. Ethanol washing and DI washing were respectively performed four times and three times using a centrifuge at 3800 rpm for 15 minutes, followed by drying in an oven at 60° C.

1-2: Amination of Blue Dye-Encapsulated Silica Nanoparticles (BD @SNP)

In order to perform cross-coupling of the carboxyl groups of BD @SNP and CPBA, the hydroxyl group (—OH) on the surface of BD @SNP was substituted with a primary amine group. That is, 100 mg of BD @SNP was added to 100 ml of ethanol and dispersed for 30 minutes using an ultrasonic disperser. Then, 1 ml of APTES (3-aminopropyltriethoxysilane) was added to an agitator, followed by reaction at room temperature for 2 hours. After the reaction, ethanol washing and DI washing were respectively performed four times and three times using a centrifuge at 3800 rpm for 15 minutes, followed by drying in an oven at 60° C., thus manufacturing aminated BD @ SNP (BD @ SNP-$NH_2$).

1-3: Joining of Aminated Blue Dye-Encapsulated Silica Nanoparticles (BD @SNP-$NH_2$) and CPBA In order to provide binding ability to glycated hemoglobin, according to a carbodiimide cross-coupling method using 1-ethyl-3[3-dimethylaminopropyl]carbodiimide hydrochloride (EDC), which is a cross-coupling agent connecting a carboxyl group and a primary amine group, 4-carboxylicphenyl-boronic acid (CPBA), which is a glycated hemoglobin-binding material, was fixed on the surface of the aminated blue dye-encapsulated silica nanoparticles (BD @ SNP-$NH_2$).

That is, in order to activate the carboxyl functional group of CPBA in an environment from which light was blocked, 3.48 mM CPBA was dissolved in 0.1 M MES (2-(N-morpholino)ethanesulfonic acid) buffer solution (pH 6.0), EDC having a final concentration of 1 mM was added thereto, and the reaction was allowed to progress for 30 minutes with agitation. Then, BD @ SNP-$NH_2$ was added, followed by reaction in an agitator at room temperature for 10 to 20 hours.

After completion of the reaction, ethanol washing and DI washing were respectively performed four times and three times using a centrifuge at 3800 rpm for 15 minutes, followed by drying at room temperature or freeze-drying, thus manufacturing a blue dye-encapsulated silica nanoparticle-boronic acid (BD @ SNP-CPBA).

Figure 6:
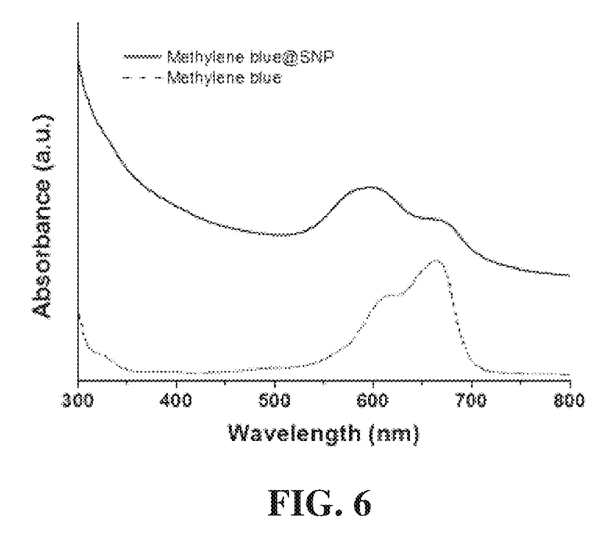
FIG. 6 is a graph showing the similarity between absorbances depending on the absorption wavelength of the "dye-encapsulated silica nanoparticle-boronic acid" manufactured according to the embodiment of the present invention and the absorption wavelength of each of the dyes that are used.
Figure 7A:
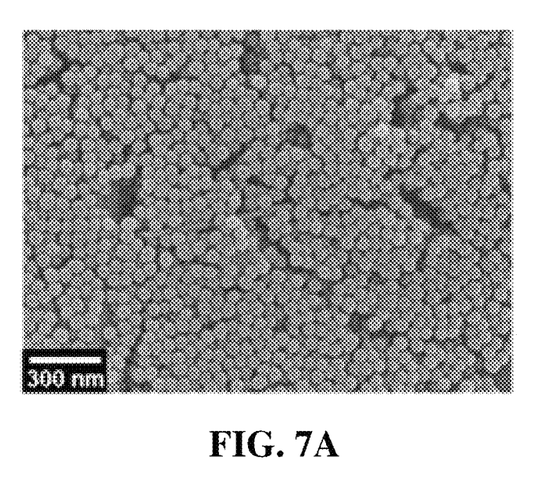
FIG. 7A shows the shape image of the "dye-encapsulated silica nanoparticle-boronic acid" manufactured according to the embodiment of the present invention, measured using a scanning electron microscope.
Figure 7B:
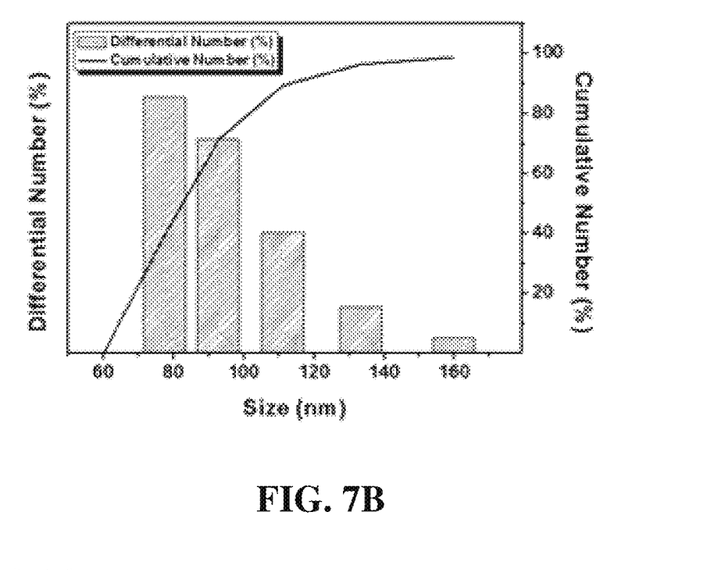
FIG. 7B is a graph showing the size thereof, analyzed using a dynamic light-scattering method.

Each of the "methylene blue" dye used in the synthesis and the "dye-encapsulated silica nanoparticle-boronic acid" was diluted with deionized water (DI water), and measurement with UV/Vis spectroscopy was then performed. As a result, as shown in FIG. 6, it can be seen that the "dye-encapsulated silica nanoparticle-boronic acid" has an inherent absorption wavelength of the blue dye even after the synthesis. With respect to this, the particles were analyzed using a scanning electron microscope and a dynamic light-scattering method. As a result, as shown in FIGS. 7A and 7B, it could be confirmed that nanoparticles having uniform morphology and a size of about 30 to 40 nm were synthesized.

Example 2: Measurement of Glycated Hemoglobin Using a Reagent Composition for Measuring Glycated Hemoglobin Containing BD @SNP-CPBA and Hemolytic Liquid 200 μl of a reagent composition containing a hemolytic liquid ($ZnCl_2$, NaCl, $MgCl_2$, Triton X-100, $NaN_3$, glycine, HEPES, pH 8.1) and BD @SNP-CPBA manufactured in Example 1 was placed in a brown tube, and 5 μl of a blood sample in which the % value of glycated hemoglobin was measured using a reference instrument (Tosoh Gil analyzer) was added thereto, followed by reaction for 2 minutes. 25 μl of the reaction solution was put on an absorption pad of a cartridge of an optical instrument (Epithod®616, DxGen) to be absorbed for 15 seconds, and 25 μl of a washing solution (morpholine, NaCl, Triton X-100, glycerol, and $NaN_3$ mixture solution) was added thereto, followed by washing for 15 seconds. Next, the optical reflectances of red total hemoglobin and blue BD @SNP-CPBA-glycated hemoglobin on the cartridge were measured in the optical instrument (Epithod®616, DxGen). The % reflectance (% R) measured for each wavelength was converted into a K/S value, which is a quantitative index of how much of the coloring material is present on the surface thereof in use, and the formula for converting the % reflectance into the K/S value is as follows.

$$K/S = \frac{(1 - \% \ R)^2}{2 \times \% \ R}$$

($K$ = absorption coefficient, $S$ = scattering coefficient)

Therefore, after the % reflectance value obtained by radiating the red light source representing the amount of glycated hemoglobin and the % reflectance value obtained from the blue light source representing the total hemoglobin were each substituted with the K/S value, the ratios thereof were calculated, thereby measuring the amount of glycated hemoglobin in the blood.

Figure 8:
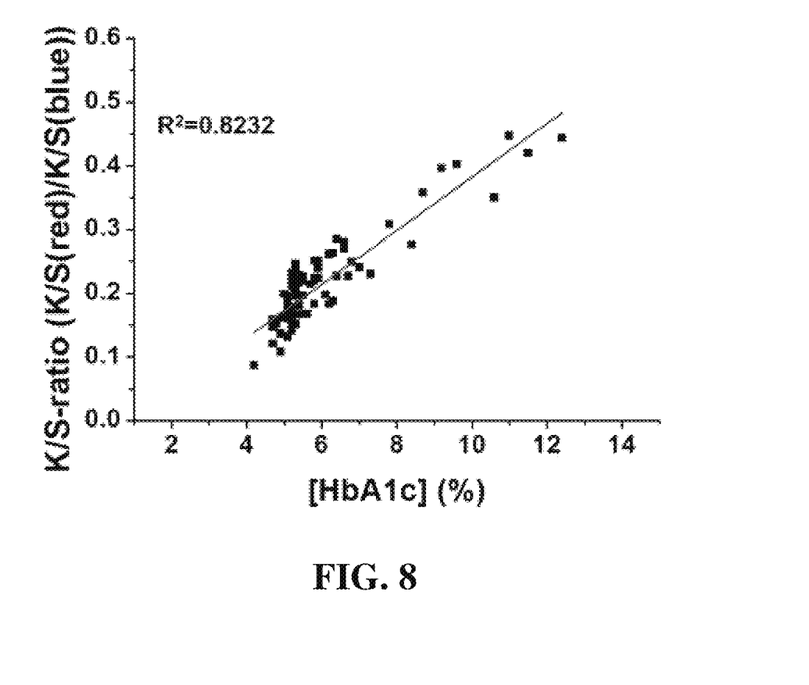
FIG. 8 is a graph showing the reflectance value of the "dye-encapsulated silica nanoparticle-boronic acid" depending on the glycated hemoglobin concentration of a blood sample, the concentration of which is known.

As shown in FIG. 8, it could be seen that, as the ratio of glycated hemoglobin contained in the blood is increased, the relative amount (K/S value) of the "dye-encapsulated silica nanoparticle-boronic acid" binding thereto is increased. Therefore, it was confirmed that the method of measuring glycated hemoglobin according to the present invention is capable of being widely used to diagnose diabetes.

Although specific portions of the present invention have been described in detail above, those skilled in the art will appreciate that this specific description is only a preferred embodiment, and that the scope of the present invention is not limited thereby. Accordingly, the actual scope of the present invention will be defined by the appended claims and their equivalents.

INDUSTRIAL APPLICABILITY

The reagent composition for measuring glycated hemoglobin according to the present invention contains a hemolytic liquid, so that the reagent composition may be reacted with glycated hemoglobin at the same time as hemolysis, thereby labeling glycated hemoglobin. Further, since glycated hemoglobin may be measured in a simple manner using an optical analyzer merely by injecting a washing liquid into a measurement cartridge without any separation process, the reagent composition is capable of being widely used to diagnose diabetes.

The invention claimed is:

1. A reagent composition for measuring glycated hemoglobin, the composition comprising:
   a hemolytic liquid; and
   boronic acid conjugated with dye-encapsulated silica nanoparticles specifically binding to the glycated hemoglobin,
   wherein the dye encapsulated in the silica nanoparticles is methylene blue.

2. The reagent composition of claim 1, wherein the hemolytic liquid is selected from the group consisting of TRIS, HEPES, TES, MOPS, and PIPES.

3. The reagent composition of claim 1, wherein the dye-encapsulated silica nanoparticles are manufactured by adding the methylene blue and silica to a mixture solution of water and a surfactant or a mixture solution of water and an organic solvent, followed by agitation and addition of a basic catalyst.

4. The reagent composition of claim 1, wherein a diameter of the dye-encapsulated silica nanoparticles is 10 to 500 nm.

5. The reagent composition of claim 1, wherein the the boronic acid conjugated with the dye-encapsulated silica nanoparticles is manufactured by aminating the dye-encapsulated silica nanoparticles, followed by conjugation with 4-carboxylicphenyl boronic acid (CPBA), or by carboxylating the the dye-encapsulated silica nanoparticles, followed by conjugation with 3-aminophenylboronic acid (APBA).

6. A method of measuring glycated hemoglobin, the method comprising:
   (a) introducing a blood sample into a reagent composition for measuring the glycated hemoglobin, the reagent composition comprising a hemolytic liquid and boronic acid conjugated with dye-encapsulated silica nanoparticles specifically binding to the glycated hemoglobin, followed by hemolysis and reaction, wherein the dye encapsulated in the silica nanoparticles is methylene blue;
   (b) injecting a resulting product from step (a) into an absorption pad of a cartridge, followed by washing with a washing liquid;
   (c) measuring an optical reflectance of the absorption pad using an optical instrument to measure amounts of total hemoglobin and the glycated hemoglobin; and
   (d) calculating a ratio of the glycated hemoglobin on a basis of the measured amounts of the total hemoglobin and the glycated hemoglobin.

7. The method of claim 6, wherein the optical instrument simultaneously radiates as light sources a wavelength for measuring the total hemoglobin and a wavelength for measuring the glycated hemoglobin binding to the boronic acid conjugated with the dye-encapsulated silica nanoparticles, thus measuring the optical reflectance.

8. A method of diagnosing diabetes, the method comprising:
   (a) introducing a blood sample of a patient into a reagent composition for measuring glycated hemoglobin, the reagent composition comprising a hemolytic liquid and boronic acid conjugated with dye-encapsulated silica nanoparticles specifically binding to the glycated hemoglobin, followed by hemolysis and reaction, wherein the dye encapsulated in the silica nanoparticles is methylene blue;
   (b) injecting a resulting product from step (a) into an absorption pad of a cartridge, followed by washing with a washing liquid;
   (c) measuring an optical reflectance of the absorption pad using an optical instrument to measure amounts of total hemoglobin and the glycated hemoglobin;
   (d) calculating a ratio of the glycated hemoglobin on a basis of the measured amounts of the total hemoglobin and the glycated hemoglobin; and
   (e) diagnosing diabetes of the patient based on the ratio of the glycated hemoglobin.

* * * * *